(12) United States Patent
Alasaarela et al.

(10) Patent No.: US 9,033,507 B2
(45) Date of Patent: May 19, 2015

(54) EXAMINATION INSTRUMENT

(71) Applicant: Optomed Oy, Oulu (FI)

(72) Inventors: Ilkka Alasaarela, Oulunsalo (FI); Jussi Soukkamaki, Oulu (FI); Ilkka Jolma, Oulu (FI); Markku Virta, Kempele (FI)

(73) Assignee: OPTOMED OY, Oulu (FI)

( * ) Notice: Subject to any disclaimer, the term of this patent is extended or adjusted under 35 U.S.C. 154(b) by 0 days.

(21) Appl. No.: 14/003,099

(22) PCT Filed: Mar. 20, 2013

(86) PCT No.: PCT/FI2013/050317
§ 371 (c)(1),
(2) Date: Sep. 4, 2013

(87) PCT Pub. No.: WO2013/140043
PCT Pub. Date: Sep. 26, 2013

(65) Prior Publication Data
US 2015/0002817 A1 Jan. 1, 2015

(30) Foreign Application Priority Data
Mar. 21, 2012 (TW) .............................. 101109592 A

(51) Int. Cl.
*A61B 3/14* (2006.01)
*A61B 3/12* (2006.01)
*A61B 3/00* (2006.01)

(52) U.S. Cl.
CPC ... *A61B 3/14* (2013.01); *A61B 3/12* (2013.01); *A61B 3/1208* (2013.01); *A61B 3/0008* (2013.01)

(58) Field of Classification Search
CPC ........ A61B 3/0008; A61B 3/12; A61B 3/107; A61B 3/1005; A61B 3/158; A61B 5/14555
USPC ........................... 351/221, 246, 206, 211, 212
See application file for complete search history.

(56) References Cited

U.S. PATENT DOCUMENTS

2002/0063851 A1   5/2002 Shibutani et al.
2003/0156258 A1   8/2003 Tanassi et al.
(Continued)

FOREIGN PATENT DOCUMENTS

DE   102007031923 A1   7/2008
EP       1929935 A1   6/2008
(Continued)

OTHER PUBLICATIONS

Official Action in corresponding Taiwanese Application No. 101109592, pp. 1-3 (Mar. 18, 2014).
(Continued)

*Primary Examiner* — Hung Dang
(74) *Attorney, Agent, or Firm* — Hoffmann & Baron, LLP

(57) ABSTRACT

Light from an exit pupil of an illumination unit is directed to a beam splitter which directs the light to an objective. The retina is illuminated, if a real image of the exit pupil of the illumination unit and a real image of an entrance pupil of a camera unit are formable in a position ranging from the cornea to the backside of the crystalline lens with the light. The objective forms a real intermediate image of the retina between the objective and the camera unit. The beam splitter directs the light from the retina to the camera unit, while causing the path of the illumination and the path of the imaging to deviate for non-overlapping images of the exit pupil and the entrance pupil in the crystalline lens. A relay lens system forms a real image of the intermediate image on a detecting component with the light reflected from the retina for transforming the image into an electric form to be shown on a screen.

22 Claims, 11 Drawing Sheets

(56) References Cited

U.S. PATENT DOCUMENTS

2006/0126018 A1* 6/2006 Liang .......................... 351/211
2006/0146284 A1 7/2006 Collins et al.

FOREIGN PATENT DOCUMENTS

| JP | 2004522488 A | 7/2004 |
| JP | EP2111785 A1 | 10/2009 |
| WO | 2009050339 A1 | 4/2009 |
| WO | WO2011029064 A1 | 3/2011 |

OTHER PUBLICATIONS

Supplementary European Search Report for corresponding International Application No. EP13763838, dated Apr. 8, 2014, 2 pages.
International Search Report for corresponding International Application No. PCT/FI2013/050317, dated Jul. 12, 2013, 4 pages.

* cited by examiner

EXAMINATION INSTRUMENT

CROSS-REFERENCE TO RELATED APPLICATIONS

This application is a National Stage application of International Application No. PCT/FI2013/050317 filed Mar. 20, 2013, which claims benefit to Taiwan Application No. 101109592, filed Mar. 21, 2012, which are incorporated by reference herein in their entirety.

BACKGROUND

1. Field

The exemplary and non-limiting embodiments of this invention relate generally to an eye examination instrument.

2. Description of the Related Art

The optical design of an fundus camera contains several challenging requirements: The image needs to be sharp and evenly illuminated with a brightness high enough to overcome noise in detection. The field-of-view should be wide enough to capture a large section of the retina. The image needs to be free from glare. Particularly reflections from lenses of the fundus camera, from the cornea and from the crystalline lens of the eye easily spoil the quality of an image. It is also desirable that imaging can be performed with undilated pupils, i.e. in a non-mydriatic way. Preferably the device should allow hand-held operation. Finally, the device should be compact and easy to align with the eye during the imaging, and the working distance needs to be long enough.

There have been attempts to build a good ophthalmoscope. In the prior art, problems related to reflections have typically been addressed by using a black-dot conjugate method together with suitable shaped forms of the lenses common to illumination and imaging. However, they impair the quality of the image by increasing aberrations, or limit the usable field-of-view. Therefore, there is a clear need for a proper ophthalmoscope.

SUMMARY

The following presents a simplified summary of the invention in order to provide a basic understanding of some aspects of the invention. This summary is not an extensive overview of the invention.

An aspect of the invention relates to an apparatus for imaging an eye, comprising: an illumination unit, a beam splitter, an objective, a relay lens system and a camera unit; the illumination unit comprising an optical radiation source, and the illumination unit being configured to direct optical radiation of the source from an exit pupil of the illumination unit to the beam splitter; the beam splitter being configured to direct the optical radiation to the objective; the illumination unit being configured to illuminate the retina of an eye with the optical radiation, and the objective being configured to form a real intermediate image of the retina between the objective and the camera unit with the optical radiation reflected from the retina, wherein a real image of the exit pupil of the illumination unit and a real image of an entrance pupil of the camera unit are formable in the position ranging from the cornea to the backside of the crystalline lens of an eye; the beam splitter being configured to direct the optical radiation from the retina to the camera unit, the beam splitter being configured to deviate the path of the illumination radiation and the path of the imaging radiation in a predetermined manner for preventing an overlap of the images of the exit pupil and the entrance pupil at least in the crystalline lens; and the camera unit comprising a detecting component, the relay lens system being configured to form a real image of the intermediate image on the detecting component with the optical radiation reflected from the retina for the optical image to be shown.

An aspect of the invention relates to a method for imaging an eye comprising: directing optical radiation of a source from an exit pupil of an illumination unit to a beam splitter; directing, by the beam splitter, the optical radiation to an objective along a path of the illumination radiation; illuminating the retina of the eye through the objective with the optical radiation such that a real image of the exit pupil of the illumination unit and a real image of an entrance pupil of a camera unit are formable in a position ranging from the cornea to the backside of the crystalline lens of the eye; forming, through the objective, a real intermediate image of the retina between the objective and the camera unit in a path of the imaging radiation with the optical radiation reflected from the retina; directing, by the beam splitter, the optical radiation from the retina to the camera unit; deviating, by the beam splitter, the path of the illumination radiation and the path of the imaging radiation in a predetermined manner for preventing an overlap of the images of the exit pupil and the entrance pupil at least on the surfaces of the crystalline lens; and forming, by a relay lens system, a real image of the intermediate image on a detecting component with the optical radiation reflected from the retina for the optical image to be shown.

Further embodiments of the invention are disclosed in the dependent claims.

The present solution enables a non-mydriatic imaging of an eye, the imaging resulting in glare-free images with a proper field-of-view.

Although the various aspects, embodiments and features of the invention are recited independently, it should be appreciated that all combinations of the various aspects, embodiments and features of the invention are possible and within the scope of the present invention as claimed.

BRIEF DESCRIPTION OF THE DRAWINGS

In the following the invention will be described in greater detail by means of exemplary embodiments with reference to the attached drawings, in which.

DETAILED DESCRIPTION

Exemplary embodiments of the present invention will now be described in greater detail hereinafter with reference to the accompanying drawings, in which some, but not all embodiments of the invention are shown. Indeed, the invention may be embodied in many different forms and should not be construed as limited to the embodiments set forth herein. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments.

Figure 1:
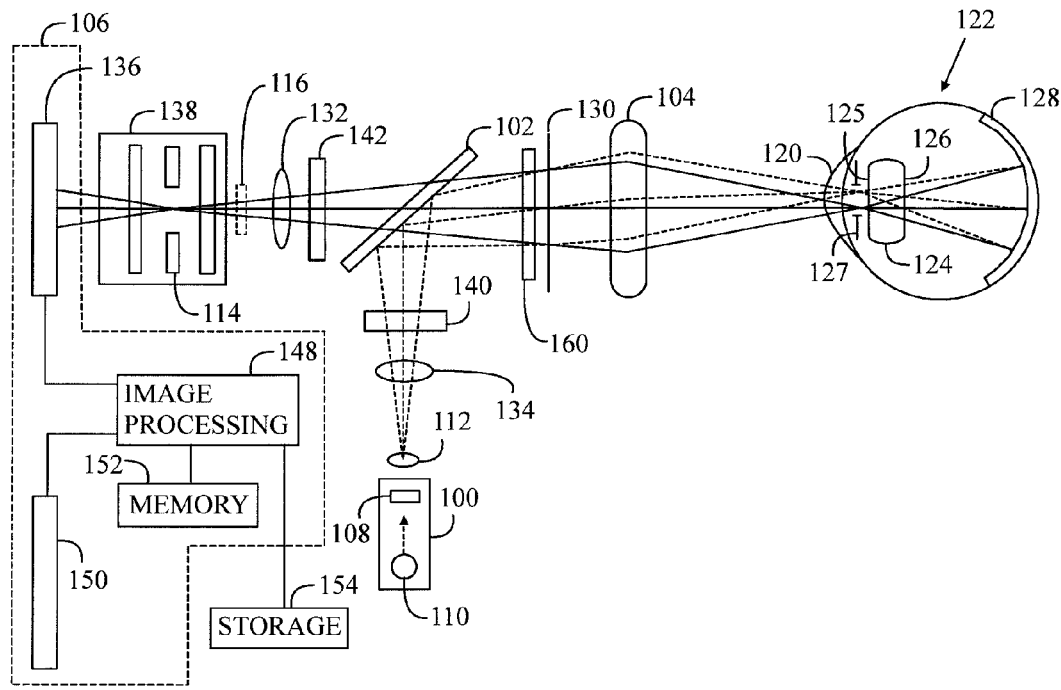
FIG. 1 shows an architecture of an eye examination instrument.

An example of an architecture of an apparatus such as an examination instrument of an eye is illustrated in FIG. 1, which is a simplified architecture only showing some elements and functional entities, whose implementation may vary. The examination instrument for imaging an eye may comprise an illumination unit 100, a beam splitter 102, an objective 104 and a camera unit 106. The illumination unit 100 comprises a lens or lenses 108 and an optical radiation source 110 which may, in turn, comprise one or more source elements. The illumination unit may transmit at least one of the following: ultraviolet light (about 250 nm to 400 nm), visible light (about 400 nm to 700 nm), infrared light (about 700 nm to 1400 nm).

The illumination unit 100 may direct optical radiation of the source 110 from an exit pupil 112 of the illumination unit 100 to the beam splitter 102. The exit pupil 112 is an image of a physical aperture in the illumination unit 100 formed by the optical elements after the aperture. The beam splitter 102 directs the optical radiation to the objective 104 in a path 134 of illumination radiation. A path of an optical radiation may be defined as a volume occupied by the optical radiation. The size and shape of the path depends on the properties of lenses and other optical elements. The eye may also have some effect on the path. In FIG. 1, the beam splitter 102 reflects a part of the optical radiation towards the objective 104.

In general, a beam splitter reflects a part of the optical radiation directed to it and allows a remaining part of the optical radiation to pass through it. Often a beam splitter splits a beam of optical radiation into two such that both beams have about the same intensity which may range from a few percents or less to almost 50% of the intensity of the original non-split beam.

In an embodiment, the beam splitter 102 may comprise a polarizer. The beam splitter 102 with a polarizer may be a polarizing beam splitter, for instance. Alternatively or additionally, there may be one or more polarizers for polarizing both the illumination radiation and the imaging radiation. The polarizer associated with the beam splitter 102 may cause the optical radiation to be linearly polarized.

The objective 104 may comprise one or more lenses. The objective 104 may have a designed property of forming a real image of the exit pupil 112 of the illumination unit 100 in a position ranging from the cornea 120 to the backside 126 of the crystalline lens 124 of the eye 122 for illuminating the retina 128 of the eye 122 with optical radiation when the examination instrument is moved to a working distance from the eye. Similarly, the objective 104 may have a designed property of forming a real image of the entrance pupil 114 of the camera unit 106 in a position ranging from the cornea 120 to the backside 126 of the crystalline lens 124 of the eye 122 when the examination instrument is moved to a working distance from the eye. Illuminating optical radiation may pass the pupil 127 of the eye when propagating to the retina 128. Similarly, the imaging optical radiation travelling towards detection may pass through the pupil 127 of the eye.

The objective 104 may also have a designed property of forming a real intermediate image 130 of the retina 128 between the objective 104 and the camera unit 106 in a path 132 of the imaging radiation which is the optical radiation reflected from the retina 128. In an embodiment, the real intermediate image 130 may be between the objective 104 and the beam splitter 102.

The beam splitter 102 may direct the optical radiation from the retina 128 to the camera unit 106. In FIG. 1, the beam splitter 102 passes a part of the optical radiation through towards detection. The beam splitter 102 may have been designed and/or positioned such that the beam splitter 102 causes the path 134 of the illumination radiation and the path 132 of the imaging radiation to deviate from each other in a predetermined manner. The deviation may prevent an overlap of the images and/or beams of radiation of the exit pupil 112 and the entrance pupil 114 at least in the crystalline lens 124.

The beam splitter 102 may reside between the objective 104 and an aperture 116 of the relay lens system 138. The beam splitter 102 may be located between the entrance pupil 114 of a relay lens system 138 and the objective 104. The entrance pupil is the image of the aperture 116 of the relay lens system 138 formed by the optical elements before the aperture 116 (projected into the object space). The beam splitter 102 may reside between the intermediate image 130 and the relay lens system 138. The beam splitter 102 may form a deviation between the illuminating optical radiation and the imaging radiation. For example, a location optically halfway between the exit pupil 114 of the relay lens system 138 and the intermediate image 130 may be possible for the beam splitter 102. Some distance between the intermediate image 130 and the beam splitter 102 may be good for avoiding dust on the beam splitter 102 which may become visible in the images, for example.

If the beam splitter 102 comprises a polarizer, the optical radiation reflected from the beam splitter 102 to the objective 104 is polarized. The polarized optical radiation then propagates to the retina 128 of the eye 122 and is reflected from the retina 128. Since the surface of the retina 128 is optically rough, the polarized optical radiation becomes at least partly depolarized. When the reflected optical radiation hits the polarizing beam splitter 102, the polarized part of the optical radiation is reflected from the beam splitter 102 towards the illumination unit 100 without being detected. However, a part of the depolarized part of the reflected optical radiation propagates through the beam splitter 102 towards detection.

In addition to or instead of a polarization beam splitter, a beam splitter with a prepolarizer 140 for the illumination radiation and a postpolarizer 142 for the imaging radiation may be used. The prepolarizer 140 may perform a linear polarization to the illuminating optical radiation 134 before the beam splitter 102. The postpolarizer 142 may also be a linear polarizer and it may be in a crossed position with respect to the prepolarizer 140 i.e. the polarization axis of the postpolarizer 142 is turned 90° with respect to that of the prepolarizer 140. In this configuration, any optical radiation having a linear polarization that passes the prepolarizer 140 may not pass the postpolarizer 142. Thus, reflections from the objective 104, for example, may not pass the postpolarizer 142 and hence may not propagate to the detecting component 106. However, a part of the depolarized optical radiation reflected from the retina 128 may pass through the postpolarizer 142 up to the detecting component 106.

The camera unit 106 comprises a detecting component 136 and may comprise a relay lens system 138. The relay lens system 138 may also be a separate component from the camera unit 106. The camera unit 106 may be an integrated combination of the detecting component 136 and the relay lens system 138 such that the camera unit 106 is a commercial product as such. The camera unit 106 may also comprise the image processing unit 148 and the screen 150 in a common frame. Alternatively, the camera unit 106 may be designed and made of separate optical components unique for the examination instrument.

The relay lens system 138 may comprise at least one lens. The relay lens system 138 may form a real image of the intermediate image 130 on the detecting component 136 with the reflected optical radiation. The detecting component 136 may comprise a plurality of pixels which may be in the form of a matrix. The purpose of the detecting component 136 may be to transform the optical image into an electric form. However, the detecting component 136 may also be a photographic film instead of an optoelectronic detector. The detecting component 136 may be a CCD (Charged-Coupled Device) cell or a CMOS (Complementary Metal Oxide Semiconductor) cell. The camera unit 106 may function like a digital camera. The image in the electric form, one or more still images or a video, may be processed in an image processing unit 148 and then presented to the user on the screen 150 of the examination instrument. The image processing unit 148 may comprise a processor and memory.

Figure 2:
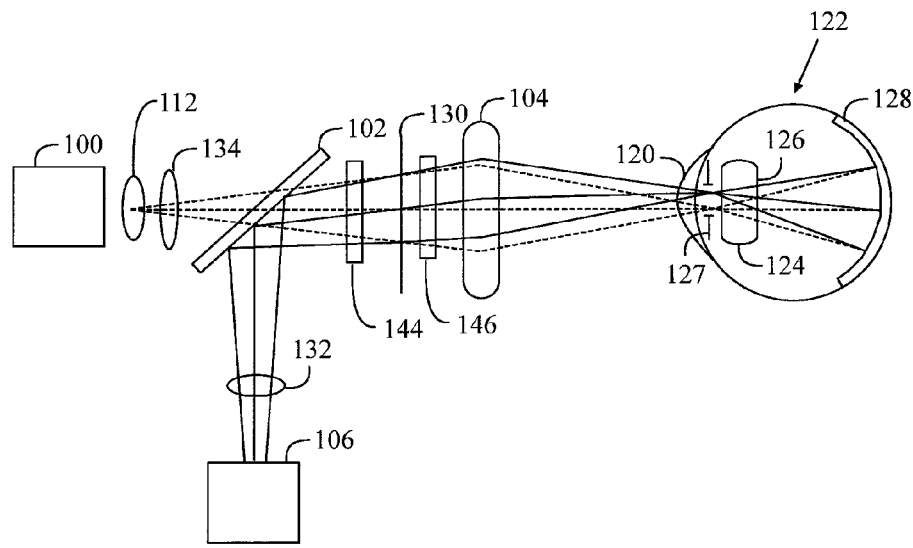
FIG. 2 shows an alternative configuration of an examination instrument of an eye.

FIG. 2 presents an alternative configuration of the eye examination device. The configuration is otherwise similar to that in FIG. 1 but the camera unit 106 and the illumination unit 100 have changed places. If the beam splitter 102 comprises a polarizer, the optical radiation passing through the beam splitter 102 to the objective 102 is polarized. The polarized optical radiation then propagates to the retina 128 of the eye 122 and is reflected from the retina 128. When the reflected optical radiation hits the polarizing beam splitter 102, the polarized part of the optical radiation passes through the beam splitter 102 towards the illumination unit 100. However, the depolarized part of the reflected optical radiation is reflected from the beam splitter 102 towards the detection.

In an embodiment which is also shown in FIG. 2, a polarization beam splitter may be replaced by a non-polarization beam splitter, a polarizer 144, and a quarterwave plate 146. The polarizer 144 may polarize the illumination radiation 134 after the reflection from the beam splitter. A quarterwave plate 146 may convert the linearly polarized illumination radiation 134 to circularly polarized radiation. The optical radiation hits the objective 104 and cornea 120 before entering the eye 122. The polarization of the optical radiation propagating towards the detecting component 106 may be returned from circularly polarized to linearly polarized radiation in the quarterwave plate 146 when it passes for the second time. However, the linear polarization is then turned by 90° with respect to the illumination radiation. Then the imaging radiation 132 may hit the polarizer 144 again. The part of the optical radiation which has maintained the polarization, particularly the reflections, may not pass the polarizer 144 because the polarization of the optical radiation has turned 90° altogether after the second pass of the quarterwave plate. However, at least a part of the depolarized optical radiation reflected from the retina 128 may pass the polarizer 144.

Examine now a little bit closer an embodiment, where the optical paths of the illuminating and imaging radiation are separated by using a polarization beam splitter instead of a mirror or a non-polarizing beam splitter. The polarization beam splitter may be used to separate the paths of the illuminating and imaging radiation far from the entrance pupil 114 of the relay lens system 138. The beam splitter with (or without) a polarizer may be included inside the examination instrument. The camera unit 106 may be an independent unit and comprise an ordinary lens or lenses, which may be used for other purposes, too.

As shown in FIG. 1, the illuminating and imaging radiation share at least the objective 104 and potentially also other lenses between the objective 104 and the beam splitter 102 which may or may not comprise a polarizer. An advantage of a shared objective 104 is that the working distance between the examination instrument and the eye 122 may be made comfortably long, which may also be beneficial for the operation of a hand-held examination instrument.

The use of a polarization beam splitter enables designing freedom for the shared lenses without disturbing reflections. When a linearly polarized illumination radiation reflected from a polarization beam splitter is reflected from the shared surfaces (the front and back surface of objective 104, for example), it preserves its state of polarization and is reflected towards the illumination unit 100 by the polarization beam splitter. However, when the illumination radiation is scattered from the retina 128, it is substantially depolarized and therefore the image of the retina 128 is transmitted through the polarization beam splitter to the detecting component 136. Naturally, the shared lenses should be substantially birefringence-free, or their birefringence should be compensated out by using suitable compensators such as a retardation plate.

In an embodiment, a mixed glare removal may be used such that the glare from the first shared surfaces may be removed on the basis of polarization, and the glare from the following (i.e. closer to the eye) surfaces may be removed on the basis of polarization with at least one compensator or by using the prior art methods, for example by designing the shapes suitably and/or using a black-dot conjugate method.

Figure 3:
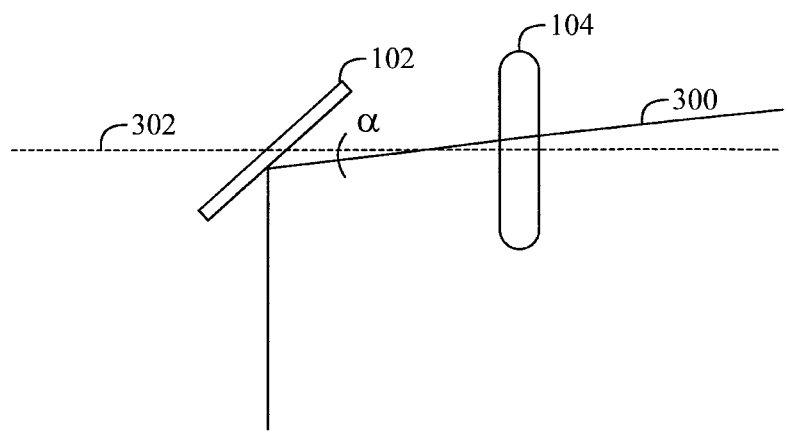
FIG. 3 shows a deviation of the axis of illumination radiation and the axis of imaging radiation.

FIG. 3 presents a deviation between the optical axis 300 of the path of the illumination radiation and the optical axis 302 of the path of the imaging radiation. FIG. 3 refers to the configuration of FIG. 1. However, a corresponding deviation in directions may be present in a configuration similar to FIG. 2, too. The angle a between the directions of the optical axis 300 of the path of the illumination radiation and the optical axis 302 of the path of the imaging radiation may be a few degrees. The angle a may be 3° to 12°, for example. The deviation is used to prevent an overlap of the images of the exit pupil 112 and the entrance pupil 114 at least in the crystalline lens 124 (see FIGS. 4 to 6). The deviation may be adjustable. The deviation may be changed by turning the beam splitter 102 or moving the illumination pupil, for example.

Figure 4:
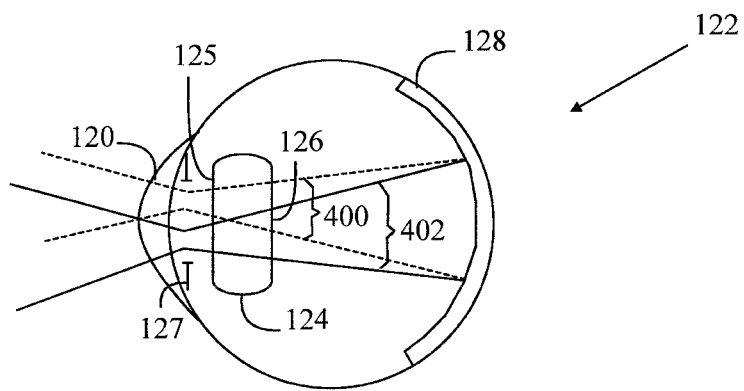
FIG. 4 shows paths of optical radiation in the eye according to the Gullstrand's principle.

Analyze now the possibilities of removing reflections caused by the eye. FIG. 4 presents optical paths in the eye in an embodiment according to the Gullstrand's principle. A common problem related to fundus cameras is the glare from the front parts of the eye. The sources of the reflections are the cornea 120 and both surfaces of the crystalline lens 124. According to the Gullstrand's principle, those reflections may be avoided by separating the paths 400, 402 of the illuminating and imaging radiations from each other on those surfaces. As shown in FIG. 4, the path 400 of the illumination radiation and the path 402 of the imaging radiation are non-overlapping on the surface of the cornea 120 and on the front surface 125 and the rear surface 126 of the crystalline lens 124. The paths converge before a narrow waist and then the paths diverge. The narrow waist between the cornea 120 and the rear surface 126 of the crystalline lens 124 means the focal point of the exit pupil 112 of the illumination unit 100. Similarly, the image of the entrance pupil 114 of the camera unit 106 is in focus at the waist of the path 402 of the imaging radiation.

Figure 5:
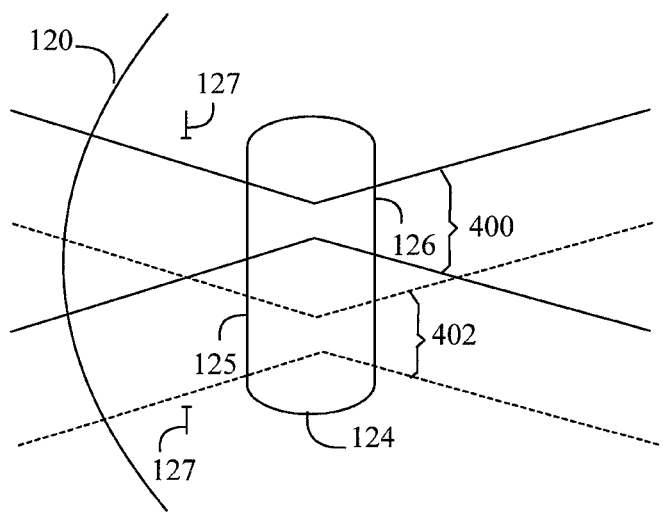
FIG. 5 shows paths of optical radiation with requirements easier than those of the Gullstrand's principle.
Figure 6:
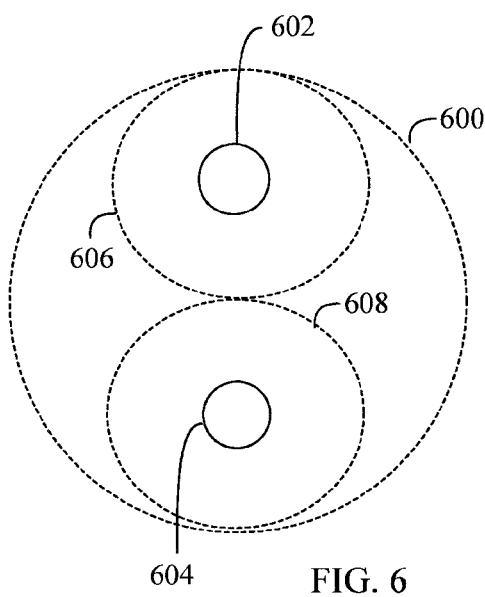
FIG. 6 shows the pupil of an eye with paths of illuminating and imaging radiations separated only in the crystalline lens.

FIGS. 5 and 6 present an embodiment, the requirements which are easier than those of the Gullstrand's principle. FIG. 5 shows the field-of-view of a configuration where the paths of the illuminating and imaging radiations are separated in a range from the front surface 125 to the rear surface 126 of the crystalline lens 124. In an embodiment where at least one polarizer like a polarizing beam splitter is used, the reflection from the cornea 120 may be eliminated or attenuated so much that the reflection does not disturb the examination or measurements of the retina. Since the reflection from the cornea 120 need not be concerned, the paths 400, 402 of the illumination radiation and the imaging radiation may only be separated on the surfaces of the crystalline lens 124, which enables a substantially larger field-of-view of the examination instrument. The real image of the exit pupil 112 of the illumination unit 100 and the real image of the entrance pupil 114 of the camera unit 106 may be designed to be in the same place or in different places on a line parallel to the optical axis of the path 134 of the illumination radiation or the path 132 of the imaging radiation.

FIG. 6 shows the pupil of an eye where the paths 400, 402 of the illuminating and imaging radiations are separated only inside the crystalline lens 124. In general, more than one path of illumination radiation may be directed to an eye. Similarly, more than one path of imaging radiation may lead from an eye to the detecting component 136. The large circle 600 represents a projection of the eye pupil to the focal plane (which is actually inside the eye). The upper circle 602 represents a projection of a path 402 of the imaging radiation on the focal plane. The lower circle 604 represents a projection of a path 400 of the illumination radiation on the focal plane. Both projections of waists of the paths may be circular discs with a diameter of approximately 1 mm (which means efficient use of the illumination and imaging optics), and there may be approximately a 1 mm distance between the paths of the radiations. The upper dashed circle 606 shows a projection of the imaging radiation at the eye pupil. The lower dashed circle 608 shows a projection of the illumination radiation at the eye pupil 600. Both paths of optical radiation fit inside the pupil 600 of the eye having a diameter of about 4 mm.

The size of a few millimetres or less may be suitable for paths of optical radiation in the use of an NIR (Near Infra Red) wavelength and visible light. The examination instrument may be aligned to a correct position for image capture, after which visible light may be used in flash mode to capture a still image or a short video. The NIR wavelength does not cause a pupillary light reflex and therefore the examination instrument may be designed to operate with larger pupil sizes.

The projections of the paths 400, 402 of the illuminating and imaging radiations may be of various sizes and shapes. They may be full or truncated circles or ellipses, rectangles or have any shape that provides the separation of the paths 400, 402 and non-vignetting behavior. The distance between the paths, the size of which depends on a desired field-of-view and a desired minimum pupil size of the eye, has substantially no optical radiation even if a small amount of optical radiation may be tolerated as long as its power is below an acceptable level. The minimum distance between paths of radiations may be 0.3 mm to 1.5 mm or up to 3 mm, for example. In FIGS. 4 to 6, the projections of the paths of the illuminating and imaging radiations are approximately of the same size, but naturally their sizes may vary depending on the brightness and optics transmission losses of the source of the optical radiation, for example. However, the required image brightness may be a liming factor when the aim is to achieve a small projection area of the paths on and in the eye.

Figure 7:
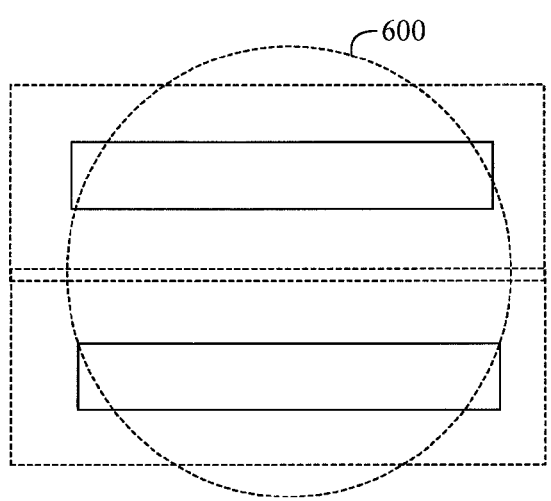
FIGS. 7 to 10 show some variations of the paths.

FIGS. 7 to 10 show some shape and size variations in the paths. In FIG. 7, the projections have rectangular shapes, for instance.

Figure 8:
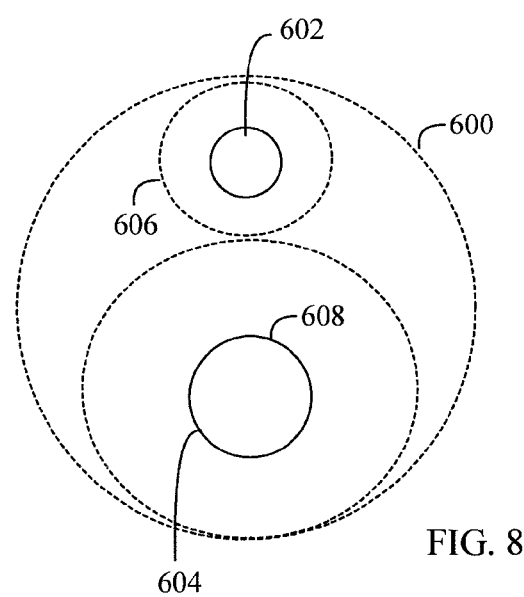

In FIG. 8, the projection of the illumination radiation is the small circle and the projection of the imaging radiation is the large circle, for example.

Figure 9:
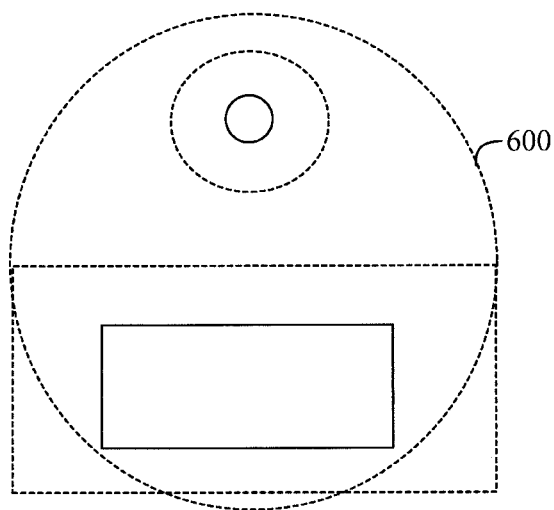

In FIG. 9, the projection of the illumination radiation is the small circle and the projection of the imaging radiation is the truncated circle which may be approximately rectangular, for example.

Figure 10:
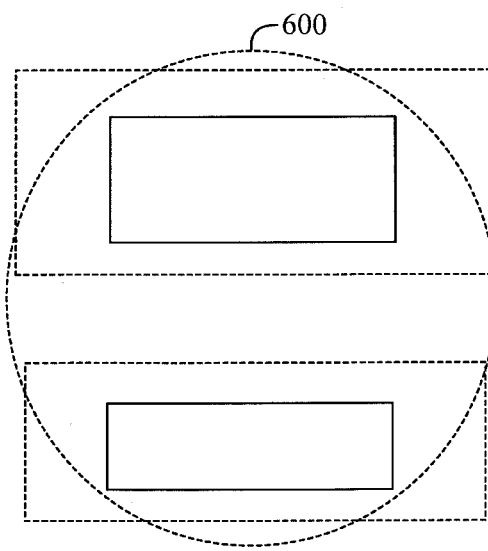

In FIG. 10, the projections of both illumination and imaging radiations are truncated circles, which may be approximately rectangular, for example.

It may be worth noticing that the alignment of the examination instrument with the eye may become easier as the alignment is more tolerant of the changes in the working distance and the lateral displacement. The required minimum diameter of the eye pupil also becomes smaller, which facilitates non-mydriatic imaging.

Figure 11:
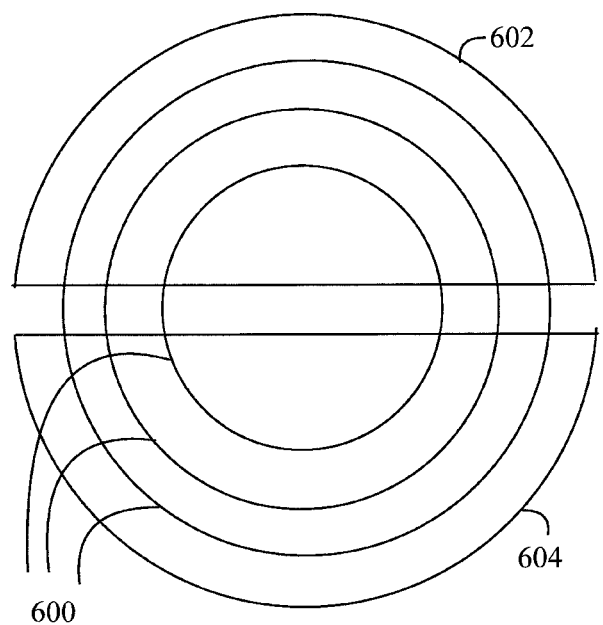
FIG. 11 shows projections of the paths of illuminating and imaging radiation larger than the pupil of an eye.

FIG. 11 shows projections 604, 602 of paths 400, 402, which are larger than the pupil of the eye 600. When the focal planes for both the illumination radiation and the imaging radiation are in the middle of the crystalline lens 124 projections of paths 400, 402 may be small enough to pass through the eye pupil in order to avoid vignetting (although some vignetting is tolerated, and actually because vignetting in paths of the imaging and illumination radiations are opposite, they can fully or partially compensate for each other to achieve an image with even illumination). Therefore the images of the exit pupil 112 of the illumination unit 100 and the entrance pupil 114 of the camera unit 106 may not be larger than necessary. However, when the examination instrument is optimized for the highest brightness mode (even to be used with dilated pupils), the focal planes for both the illumination radiation and the imaging radiation could lie substantially in the eye pupil location (as it is in the case of FIG. 11), and by so avoiding the vignetting, the sizes of the images of the exit pupil 112 of the illumination unit 100 and the entrance pupil 114 of the camera unit 106 may be larger than the pupil of the eye. Unvignetted beams of radiation may then be provided irrespective of the size of the pupil of the eye. Of course, the distance between the paths 400, 402 may need to be longer in order to achieve the same full field-of-view as with the set-up having projections of illumination radiation and imaging radiation smaller than the pupil of the eye.

Figure 12:
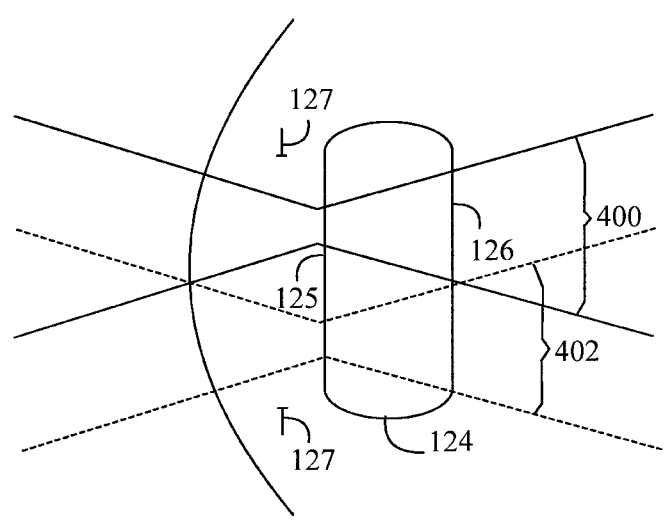
FIG. 12 shows an example where the pupil of an eye is small.

FIG. 12 shows an example where the pupil of an eye is small. In order to achieve a wide full field-of-view (for example wider than 20° or 30°) with a small eye pupil, the diameter of which may be as small as approximately 2 mm, the focal plane (i.e. waists of paths of radiations) may be close to the eye pupil. This minimizes the vignetting. The images of the exit pupil 112 of the illumination unit 100 and the entrance pupil 114 of the camera unit 106 may be so small that they both fit inside the pupil of the eye, or they may be larger. In an embodiment, the focal plane may be 0.1 mm to 0.5 mm away from the pupil of the eye inside the crystalline lens 124, and the vignetting may be compensated for by opposite vignetting in the paths of the illuminating and imaging radiations. This set-up enables the imaging of the fundus with continuous visible light, for example white light, without dilating the pupil. Imaging may take place in the form of still images or a video.

Figure 13:
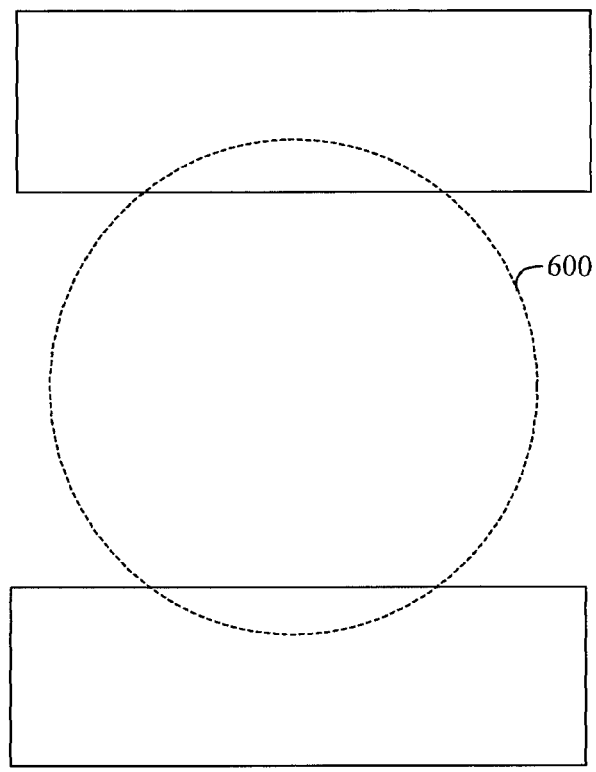
FIGS. 13 to 14 show the projections of paths of the illumination radiation and imaging radiation on the pupil of an eye.
Figure 14:
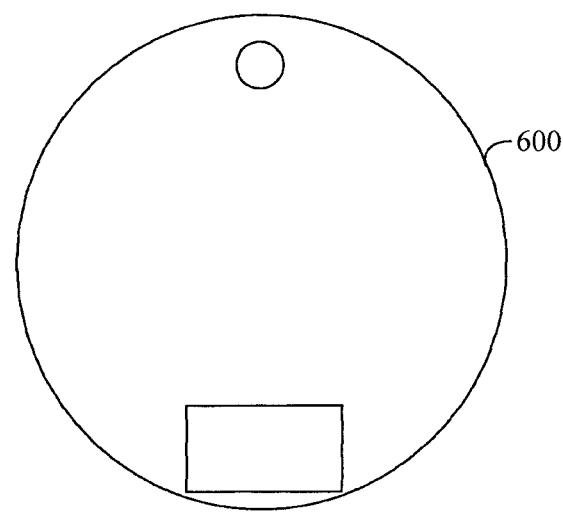

FIGS. 13 and 14 show projections of paths of the illumination radiation and imaging radiation on the pupil of an eye. In FIG. 13 the projections have rectangular shapes, which are larger than the pupil of an eye, for instance. In FIG. 14 the projection of the illumination radiation is the small circle and the projection of the imaging radiation is the smaller rectangle, for example.

An eye has substantial birefringence between the cornea 120 and crystalline lens 124. Hence, the reflections from the crystalline lens 124 will become visible if the paths 400, 402 of the illumination radiation and the imaging radiation are not separated in the crystalline lens 124. However, in some embodiments, those reflections may be avoided by using a polarization compensator such as at least one retardation plate, which may also be adjustable. The compensator may compensate for the corneal birefringence and thus the paths 400, 402 need not to be separated at the cornea 120. As a result, the étendue of the optical instrument is maximized. The maximized étendue means that optical power directed into the eye may be optimized to be sufficiently high and the collecting power of the examination instrument may be increased. The maximized étendue provides advantages such as increased brightness and a larger field-of-view, for example.

In an embodiment, the polarization state of light may be mixed or modulated in a desired manner and/or degree by using a polarization scrambler or a suitable (possibly adjustable) compensator, before the light enters into the eye 122. The paths of the illumination radiation and the imaging radiation may be separated in a range from the cornea 120 to the rear surface 126 of the crystalline lens 124. That enables the polarization-dependent properties of the retina 128 to be imaged, measured or eliminated.

We can have a closer look at the illumination unit 100 now. The exit pupil 112 of the illumination unit 100 may be defined as an illumination pupil, i.e. the real or virtual pupil from which the illumination radiation seems to be originate when viewed from outside of the illumination unit 100, such as from the beam splitter 102. The exit pupil 112 of the illumination unit 100 may have different forms and sizes. In an embodiment, the illumination pupil may be circlar, but it can be elliptical, rectangular, a truncated circle or a truncated ellipse as well. When the device is optimized for a small pupil of an eye (particularly less than 3 mm diagonally) the illumination pupil may be unvignetted although the brightness may vary from point to point in images of retina.

The path of the illumination radiation from the exit pupil 112 of the illumination unit 100 may have a diverging shape, and the illumination radiation illuminates a required portion of the intermediate image plane substantially uniformly. The required portion is the same as the conjugate image of the full-field-of-view area of the retina 128. The light outside the required area may be blocked in order to avoid stray light. The blocking may be carried out as early as possible, for example by adding vignetting baffles inside or after the illumination unit 100 or by designing and using a field stop inside the illumination module (may also be called as illumination field stop). In addition to the stray light blocking, the illumination field stop may be used for shaping the illumination on the retina 128. The illumination may be shaped in a circular, elliptical, or line form, for example. Also other shapes are possible. The ellipse, the line and the like may have different orientations. The illumination field stop may comprise a changeable aperture, such that the user may change the illumination size and shape on the retina. Still another possibility is to use spatial modulator, such as LCD (Liquid Crystal Display), LcoS (Liquid crystal on Silicon) or DMD (Digital Micromirror Device) micro-display, which may modulate electrically the size and shape, or even the wavelengths, of the illumination of the retina 128.

Examine now the illumination unit 100. In an embodiment where more than one element is utilized, each of the elements may transmit a predetermined band of optical radiation. The optical band may vary from a single wavelength to hundreds of nanometres or even thousands of nanometres. In an embodiment, the optical radiation source 110 may be a single element whose optical band may be controlled. The bandwidth and the mean wavelength may be altered in a predetermined manner. The control of the band may be performed electrically. For example, the mean wavelength may be altered by electrically changing the generation of optical radiation in the element.

In an embodiment, the optical radiation source may comprise a wideband source element and a tunable filter. The output band of the optical radiation source may be selected on the basis of the filter. The filter may have a plurality of filter elements, each filter element passing through a different band or a different group of wavelengths. Each of the filter elements alone or several filter elements together may be used to select the output wavelengths of the illumination unit 100. The tunable filter may also be tuned to pass a desired optical band or desired optical bands electrically by changing its optical properties.

The illumination unit 100 may comprise lenses, lightpipes, dichroics, mirrors, apertures etc. needed for forming the exit pupil 112 of the illumination unit 100 and a suitable illumination to the plane of the intermediate image 130. A source element may be, for example, a LED (Light Emitting Diode), an organic LED, light emitting plasma, a laser, an incandescent bulb, a halogen bulb, an arc lamp (such as a Xenon arc lamp, for example), a fluorescent lamp, or any lamp emitting suitable wavelengths and having other suitable properties for the device.

In an embodiment, the illumination unit 100 comprises one white LED chip and one LED chip emitting at near-infrared (NIR) wavelength, the radiations of which may be combined together by using a dichroic mirror, for example. The white LED chip may emit visible light in a band of 400 nm to 700 nm and a NIR LED chip may emit light in a band of 700 nm to 1200 nm or in a narrower band of 800 nm to 900 nm, for instance. By using the NIR wavelength the examination instrument may be aligned to a correct position for image capture after which the white light may be used in flash mode to capture a still image or a (short) video. The NIR wavelength does not cause a pupillary light reflex and therefore the examination instrument may be designed to operate with larger pupil sizes, which, in turn, facilities to the balancing of the compromises in the optical design.

In an embodiment, the eye is illuminated only with near infrared radiation and the optical examination device is kept out of focus with the near infrared radiation in such a way that visible light would be in focus. Such a setting of the optical components, i.e. focusing, is possible because lenses refract near infrared radiation a little bit differently from the visible light and the difference in refraction and hence in focusing is known beforehand. When visible light is flashed, there is no need to take actions for focusing because the imaging optics is already in a focused state.

For many diagnostic purposes, such as in fluorescent angiography, it may be beneficial to illuminate and/or image with predetermined optical bands. In that and other spectral analysis purposes the illumination unit 100 may comprise one or more sources which transmit wide-band optical radiation, which may then be filtered by using bandpass filters to provide at least one desired wavelength band. In fluorescent angiography, suitable illumination could be between 465 nm and 490 nm, for example. The use of filters may be avoided when using one or more source elements which may emit the light in one or more suitable wavelength ranges. An example of such filterless embodiment is a blue LED emitting at a central wavelength of 470 nm for angiography. In an embodiment, wavelength-tunable filters may be used.

It may also be useful to filter the imaging optical radiation before it reaches the detecting component 136. The filtering may limit the imaging optical radiation to at least one desired band. The bandwidth of the at least one band may vary from a single wavelength (a very narrow notch filter) to hundreds of nanometres, for example. However, the bandwidth of the optical band or bands is not limited to the example.

Filters may also be needed to block one or more optical bands in an IR or a UV domain. For instance, UV radiation may cause damage in the eye. Separate filters may be used in the path of the imaging radiation and the path of the illumination radiation for obtaining at least one image with a partially or fully different band than that of the illumination.

In an embodiment, the illumination unit 100 may be based on teachings of Köhler illumination although critical illumination or some other illumination scheme may be used, too. The emitting area of a LED chip may be imaged to the exit pupil 112 of the illumination unit 100 (i.e. the illumination pupil). The angular output of the chip imaged at the illumination field stop 160 may then be imaged to a plane of the intermediate image 130, which may be imaged to the retina 128 by the objective 104. Besides the advantage of having an illumination field stop for blocking offensive stray light, this may provide a well-defined illumination pupil and uniform and non-vignetted illumination to the retina 128.

In an embodiment, a simple illumination may be based on an aspherical condenser lens, which collects light from a LED and images the emitting area into the exit pupil 112 of the illumination unit 100 and at the same time images the illumination field stop 160 to the plane of the intermediate image 130.

In an embodiment, the illumination unit 100 may comprise a LED with collecting optics or a LED chip alone.

Examine now the objective 104 a little bit closer. The examination instrument may comprise the objective 104 and the relay lens system 138. The objective 104 may form a real intermediate image 130 of a retina 128 between the objective 104 and the detecting component 136. The relay lens system 138 may form an image of the intermediate image 130 on the detecting component 136. This imaging that takes place twice, or double imaging, where the intermediate image 130 is imaged, may bring advantages: For example, there is space for the beam splitter 102. Otherwise, the beam splitter 102 should be inserted outside the objective 104, i.e. between the objective 104 and the eye 122. That could cause severe drawbacks, such as a short working distance to the eye, a narrow field-of-view and problems related to image brightness.

Alternatively, the beam splitter 102 could be inserted into the objective 104, which restricts the objective design considerably and causes other drawbacks, such as a large required size for the detecting component 136. Another advantage of the double imaging architecture may be that the magnification from the retina 128 to the detecting component 136 is easy to adjust and set to a suitable value for a desired size of the detecting component 136. The magnification may also be adjustable, i.e. the system may contain an optical zoom-function, by adjusting the optical elements or possibly adjusting the distance between the intermediate image 130 and the detecting component, for example. Still another advantage of the twofold imaging architecture may be that the intermediate image 130 may or may not be sharp, which means that all the aberrations caused by the eye 122 and the objective 104 need not be corrected by the objective 104 alone. Some of the aberrations may also be corrected in the relay lens system 138 instead, since the possibilities to correct aberrations with the objective 104 are limited. Hence, it may be possible to obtain a sharp image with a wide field-of-view.

Figure 15:
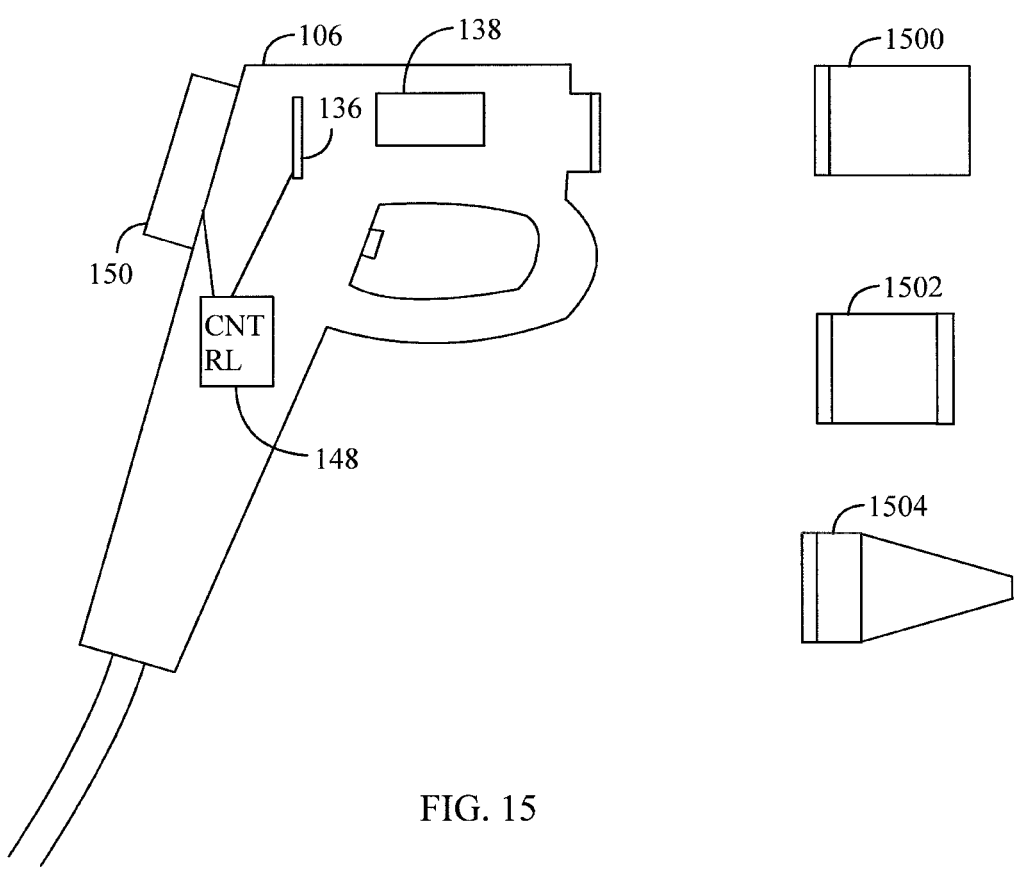
FIG. 15 shows a camera unit with optical functional parts.

Yet another advantage of the double imaging architecture is that the camera unit 106 with the relay lens system 138 and the detecting component 136 may be a part in a set which additionally comprises optical functional parts 1500 to 1504 repeatedly attachable to and detachable from the camera unit 106. Such an examination instrument is shown in FIG. 15. The camera unit 106 alone may be used in a wide range of applications, such as in the examination of outer parts of a body, for example the skin. One optical functional part 1500 may then include the beam splitter 102 and the objective 104, for example. At least one further optical functional part 1502 (or 1504) in the set may capture images of at least one organ different from both the eye 122 and the at least one organ on the outer surface of a body.

The objective 104 in its simplest form may be a singlet, which may have one or two aspherical surfaces. The angle between the optical axis of the objective 104 and the optical axis of the imaging radiation may be between 0 and 9 degrees, for example, without restricting thereto.

The objective 104 may be made of glass or optical plastics. Birefringence may be minimized by annealing the glass of the objective 104 after grinding. In an embodiment, the objective 104 comprises a doublet, which may be used to minimize chromatic aberrations. Naturally, the number of elements is not limited to one or two and a plurality of variations of the designs may exist. If some of the lenses are introducing birefringence, it is possible to use a suitable compensator to compensate for the birefringence. Another possibility is to use an objective of a suitable surface shape. Yet another possibility is to apply a black-dot conjugate method.

The focal length of the objective 104 may vary from 10 mm to 50 mm, for example. A full field-of-view may be from 20° to 60°, for example. The working distance to the eye may be from 8 mm to 40 mm, for example. The magnification from the retina 128 to the intermediate image 130 may be from 1.2 to 2.0, for example.

The relay lens system 138 may form an image of the intermediate image 130 to the detecting component 136. The beam splitter 102 with or without polarization effect may be between the intermediate image 130 and the relay lens system 138, but it may be inside the relay lens system 138, too. However, the beam splitter 102 may not be placed between the detecting component 136 and the aperture stop of the relay lens system 138, where the aperture stop acts as the entrance pupil 114 of the camera unit 106. It may be considered as an advantage that the relay lens system 138 and the objective 104 may be a separate lens systems, i.e., the detecting component 136 and the relay lens system 138 together may form a multipurpose camera unit 106 of its own.

The size and shape of the aperture stop, i.e. the entrance pupil 114 are dimensioned such that a desired image of it to the front part of the eye 122 may be provided. In an embodiment, the relay lens system 138 is a conventional camera lens system with a circular aperture. In an embodiment, the focal length of the relay lens system 138 may be between 8 mm and 100 mm. Often a focal length of 12 mm to 35 mm is found satisfying.

In an embodiment shown in FIG. 1, the examination instrument may have a field lens 160 for field flattening or for a pupil matching purpose, for example. The field lens 160 may be close to the plane of the intermediate image 130. The field lens 160 may be a part of the objective 104 or the relay lens system 138, or it may be partly common to both of them, too.

Figure 16:
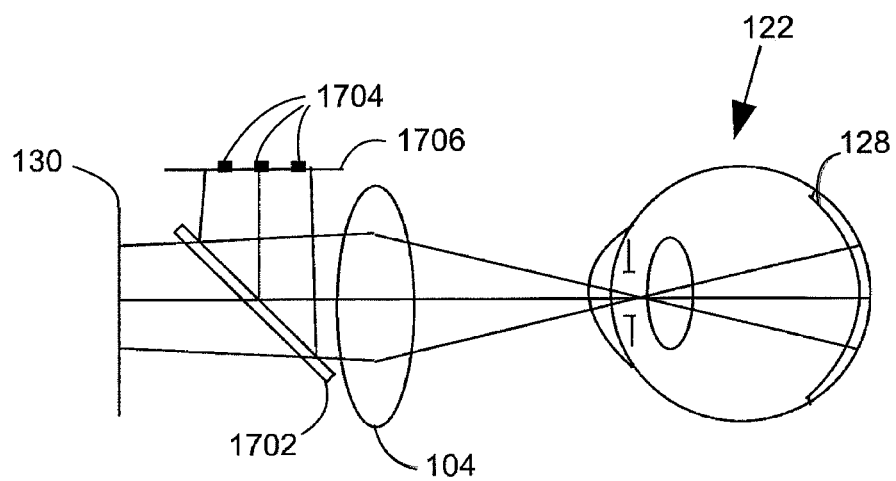
FIG. 16 shows fixation targets and their projection on the retina.

As shown schematically in FIG. 16, in an embodiment the examination instrument may comprise a beam splitter 1702 between the objective lens 104 and the intermediate image 130 and one or more fixation targets 1704 positioned substantially on the virtual mirror image 1706 of the intermediate image 130 through the beam splitter 1702. The beam splitter 1702 may correspond to the beam splitter 102. The fixation targets 1704 may be used to guide the viewing direction and the focus distance of the patients eye 122 in order to aid capturing of one or more images of the retina 128 centered to different parts of the retina and to aid focusing the device to the retina.

Figure 17:
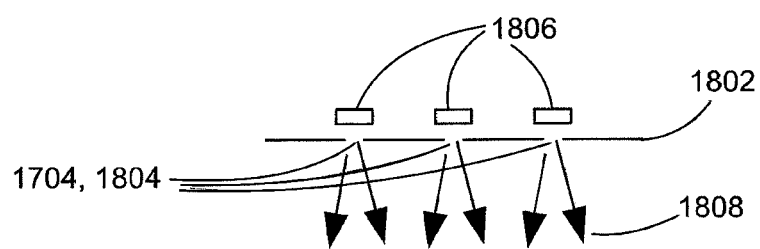
FIG. 17 shows a structure of fixation targets.

As shown in FIG. 17, the one or more fixation targets 1704 may comprise an aperture plate 1802 having apertures 1804 illuminated by one or more source units 1806, such as LEDs emitting visible radiation 1808 through the holes 1804, for example. One or more source units without aperture plate can be used as fixation target, too. The beam splitter 1702 may be a glass plate, for example which reflects a part of the emitted radiation 1808 to the eye. The beam splitter 1702 may have a suitable coating on it.

Figure 18:
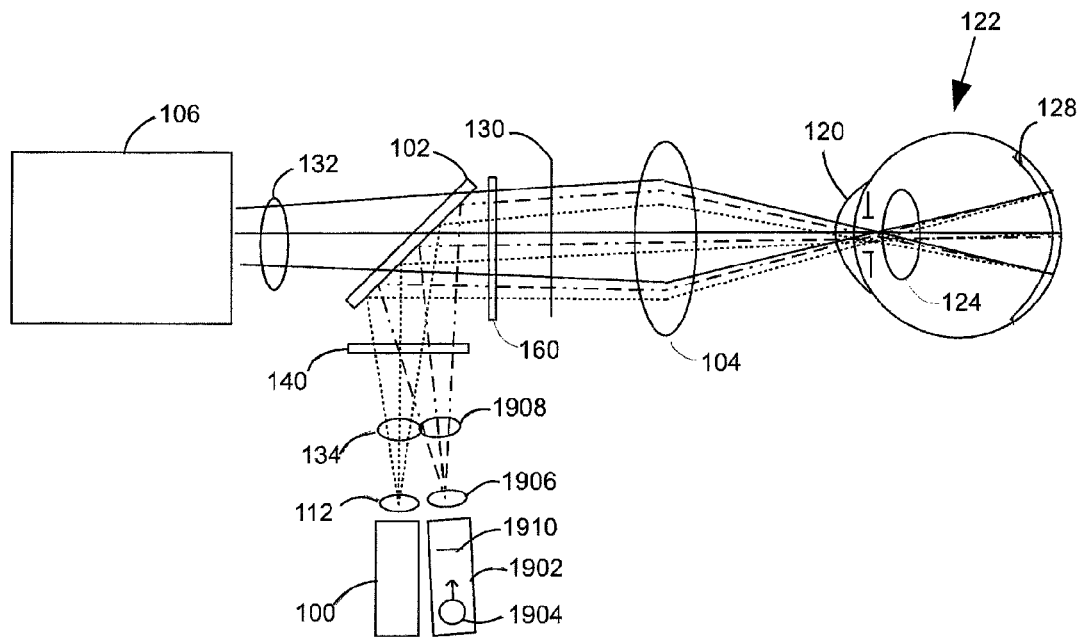
FIG. 18 shows an examination instrument with fixation targets.

Another embodiment comprising a fixation target is shown in FIG. 18, which is otherwise similar system described with FIG. 1 but has an additional second illumination unit, which may create one or more fixation targets visible for the eye 122 and which may be called a fixation target unit 1902. Similar to the first illumination unit 100, the fixation target unit 1902 may comprise optical components such as a lens or lenses and an optical radiation source 1904, which may comprise one or more source elements. The optical radiation source of the fixation target unit may operate in a visible light region such that one or more images of the fixation targets may be seen by the patient. The optical radiation may be generated by LED chips emitting red, green, blue or white radiation, for example.

The fixation target unit 1902 may direct optical radiation of the source 1904 from an exit pupil 1906 of the fixation target unit 1902 to the beam splitter 102. The exit pupil 1906 may be an image of a physical aperture in the fixation target unit 1902 formed by the optical elements after the aperture. The beam splitter 102 may direct the optical radiation to the objective 104 in a path 1908 of fixation target radiation. The beam splitter 102 may reflect a desirable part of the optical radiation via the objective 104 to the eye 122. The same principle of constructing the fixation target shown in FIG. 18 may be applied to the embodiment described in FIG. 2, or to other described embodiments, too.

The fixation target unit 1902 may comprise a field stop 1910, which may contain fixation targets the images of which may be seen by patient's eye 122, and which may be used to direct patient's eye to the desired direction. When a purpose is to have an image covering 180° of the inner horizontal surface of an eye, it may be necessary to capture three images each of which covers 60°. A first image may be captured when the person is guided to watch to the left, a second image may be captured when the person is guided to watch straight ahead, and a third image may be captured when the person is guided to watch to the right. A panorama image may be formed from the three images. The images of the fixation targets may also be used to guide an eye to accommodate to a desired distance. Typically the field stop 1910 may be conjugated with the intermediate image 130 and the retina 128 such that the patient will see the target images in focus. Because the eye typically tries to focus to visible images, the fixation targets at the field stop 1910 guide eye 122 to focus to the predetermined distance.

Figure 19:
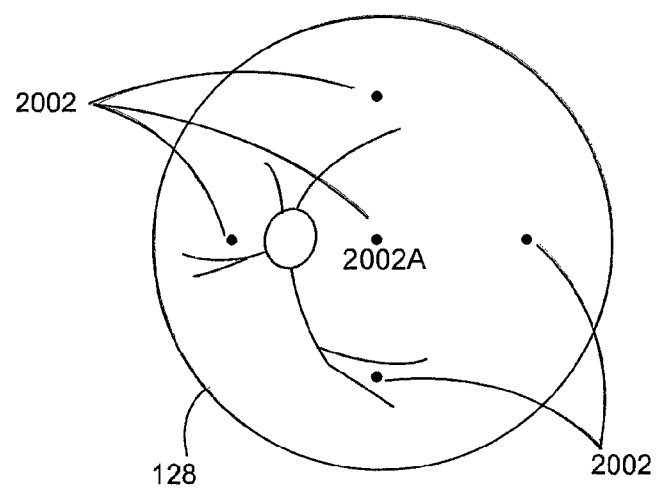
FIG. 19 shows images of fixation targets on the retina.

FIG. 19 shows an exemplary of real images of the fixation images formed by the fixation target unit 1902 on the retina 128. The images may comprise five circular spots 2002 in predetemined locations: one spot 2002A may be located on the device axis, and the other spots 2002B may be separated from the device axis by a certain distance which may be determined by a field angle. The separation field angle may be arranged to be from 8° to 25°, for example. The field angle may depend on the used field-of-view of the examination device. Each spot 2002 may be formed by a separate light source unit. The one or more light source may output one spot 2002 at a time such that the eye 122 sees only one spot 2002 at each moment and gets focused to that spot. More than one spot 2002 may also be output at a time by the light source. Then the eye 122 may see several spots 2002 at each moment and get focused to them.

The fixation target unit 1902 need not be radiating light during the image capture. Therefore possible reflections from the cornea and crystalline lens of the eye may not be disturbing image quality and thus the size and position of the exit pupil 1906 of the fixation target unit 1902 need not to be arranged as carefully as the size and position of the exit pupil 112 of the illumination unit in respect to the entrance pupil 114 of the camera unit 106. Inside the eye, the exit pupil 1906 of the fixation target unit 1902 may be imaged approximately between the images of the exit pupil 112 and the entrance pupil 114, or approximately above the image of the entrance pupil 114, for instance.

In an embodiment, the fixation target unit 1902 and the illumination unit 100 may use separate beam splitters 102 for guiding the illumination beam 134 and the fixation target beam 1908 to the eye. In FIG. 18, the fixation target unit 1902 may use the same optional pre-polarizer 140 as the illumination unit 100. However, they can use separate pre-polarizers, too. The fixation target unit 1902 and the illumination target unit 100 may also share other common components too, such as fold mirrors, lenses, or printed circuit board or heat sink for LEDs, to name a few.

Figure 20:
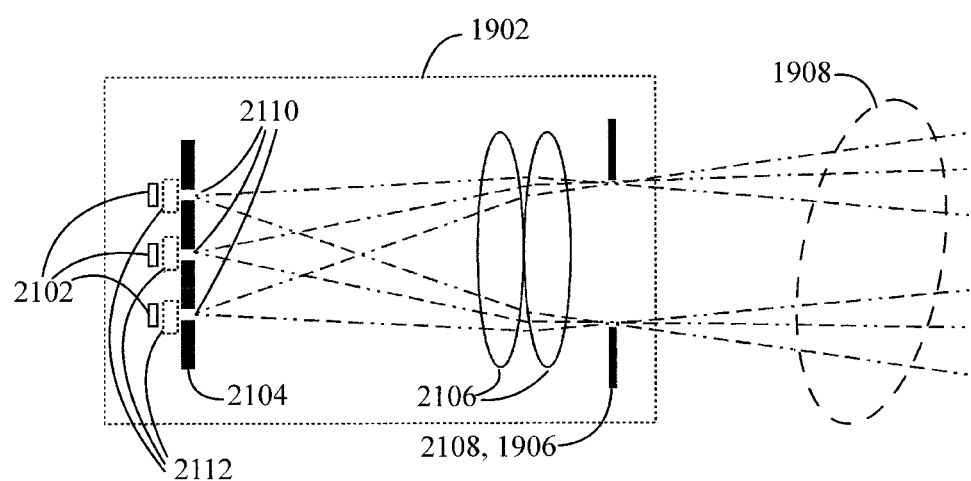
FIG. 20 shows a structure for providing fixation targets.

Let us now take a closer look of an embodiment of a fixation target unit 1902 as shown in FIG. 20. A fixation target unit 1902 may comprise one or more LED sources 2102, a hole plate 2104, one or more relay lenses 2106 and an aperture pupil stop 2108. The LED's 2102 may illuminate the holes 2110 in the hole plate 2104 for imaging the holes 2110 by the relay lens 2106 via the intermediate image 130 to the retina 128. The hole plate 2104 may be located at the field stop 1910 of the fixation target unit 1902. The path of fixation target radiation in this configuration is shown by lines 1908.

In an exemplary case the physical aperture pupil stop 2108 coincides with the exit pupil 1906 of the fixation target unit 1902, but they could also be different. If the aperture pupil stop 2108 is located between the hole plate 2104 and at least one relay lens 2106, the aperture pupil stop 2018 doesn't need to coincide with the exit pupil 1906 of the fixation target unit 1902. The aperture pupil stop 2108 may also be formed by the clear aperture of a relay lens such that a separate physical aperture may not be needed.

The aperture pupil stop 2108 may comprise an adjustable iris diaphragm, which may be used to adjust the brightness of the fixation target images without affecting the shape of the features. The brightness may be adjusted by adjusting the brightness of the output of the radiation sources, too. The brightness adjustment of the target images may be used for opening and closing the iris 127 of the eye 122. The inspection of an eye is easier when the pupil is large. Also more optical radiation may be fed into the eye of a large pupil. Furthermore, the mechanical and optical adjustment of the examination instrument is easier when the pupil of an eye is large.

There may be one or more homogenizing or diffusing elements 2112 between the LEDs 2102 and the hole plate 2104, or inside the holes 2110, in order to homogenize the light distribution of the viewed area inside the holes 2110. In that way, the structure of the LEDs is not seen by the examined person. Another possibility is to use long enough holes which act as small light pipes for providing a uniform spatial output. Still another possibility may be to feed the light from the LEDs 2102 to optical fibers which mix the distribution of the light. The fibers may then output the light towards the beam splitter 104.

Instead of circular spots, the fixation targets may provide any image on the retina. The images may comprise lines, crosses, rings, characters, numbers, symbols, or the like. The images of fixation target may be monochromatic or have different colors. In an embodiment, the field stop 1910 of the fixation target unit may be fully illuminated and the aperture hole 2104 may be changeable such that the operator may choose a desired fixation target features for each task. Additionally or alternatively, the images of the target fixation may be formed by a LED matrix, or OLED-matrix (Organic LED) which may operationally be similar to the hole plate 2104. In an embodiment, the target images may be formed by an illuminated micro-display such as LCD or LcoS (Liquid crystal on Silicon), for example, or a micro-mirror array such as DMD (Digital Micromirror Device) for example, which provide easy modulation of the target images. In an embodiment, the target images may form various patterns or arrays on the retina, such as line arrays, spot matrices, and polar arrays, for example. Any of them alone or together with others may be used as focusing aid for the examination device, or utilized for dimension or shape measurement or analysis of the eye.

The one or more fixation targets imaged on the retina may be modulated various ways. The one or more fixation targets may be continuously imaged on the retina. In an embodiment, the fixation targets may otherwise be imaged continuously on the retina but be switched off during an image capture. The one or more fixation targets may repeatably be flashed with a desired frequency on the retina, and the flashing rate may be synchronized with the image capture frequency, for example. During a video capture, the one or more fixation targets may be imaged on the retina between each frame captures so that the patient may see the fixation targets but they may not be captured in the video. In an embodiment, the one or more fixation targets may be shown in short time intervals and the captured frames including the images of one or more fixation targets may be removed from the final video sequence.

In an embodiment, the position of the field stop 1910 of the fixation target unit 1902 may be adjustable in axial direction such that the eye 122 may be guided to focus to different distances on the basis of the position of the fixation unit 1902. The field stop position adjustment may be matched with the focusing of the camera unit, too. In an embodiment of the invention, the movable field stop 1910 of the fixation target unit 1902 may be used to test or measure the accommodation of the eye 122 and or the accommodation range of the eye. The fixation target images may be adjustable in the direction perpendicular to optical axis, for example such that the operator may freely guide the patients eye viewing direction without being restricted to the predetermined positions.

Still, in an embodiment, the fixation target may contain a source unit operating in IR region. Thus, the target images may be formed by the IR light and they may be used for refractometric measurements of eye.

Generally, the focal length of the objective 104 may be between 23 mm and 27 mm, for instance. The working distance (i.e. the distance from the cornea to the nearest surface of the objective lens) of the examination instrument may be between 18 mm and 26 mm, for example. The optical distance from the illumination pupil to the intermediate image 130 may be between 90 mm and 130 mm, for example. The optical distance from the entrance pupil of the relay lens to the intermediate image is the same as the optical distance from the illumination pupil to the intermediate image within 10 mm. The focal length of the relay lens system 138 may be between 15 mm and 25 mm, for example. The diameter of the entrance pupil 114 may be between 3 mm and 6 mm. The intermediate image 130 may be approximately 18 mm to 30 mm away from the objective 104. The full field-of-view of 45° may correspond to the intermediate image diameter of about 12 mm to 22 mm.

Figure 21:
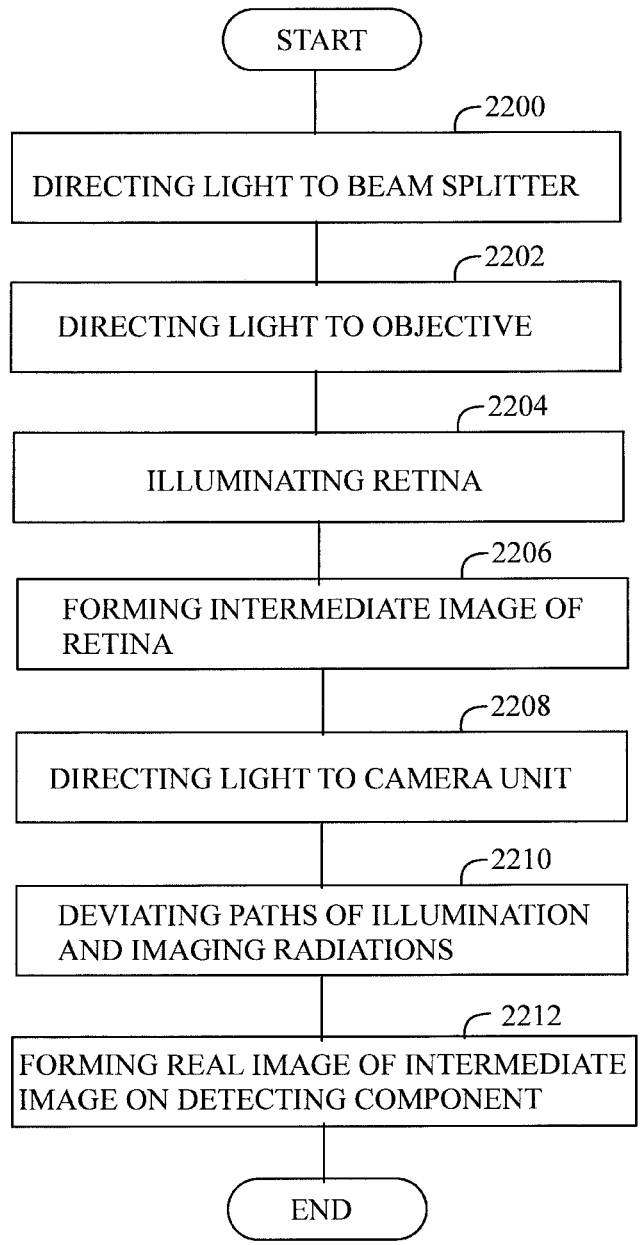
FIG. 21 shows a flow chart of a method.

FIG. 21 is a flow chart of an apparatus according to an embodiment of the invention. In step 2200, optical radiation of a source 110 is directed from an exit pupil 112 of an illumination unit 100 to a beam splitter 102. In step 2202, the optical radiation is directed to an objective 104 along a path 134 of the illumination radiation by the beam splitter 102. In step 2204, the retina 128 of an eye 122 is illuminated such that a real image of the exit pupil 112 of the illumination unit 100 and a real image of an entrance pupil 114 of a camera unit 106 are formable in a position ranging from the cornea 120 to the backside 126 of the crystalline lens 124 of the eye 122 through the objective 104 with the optical radiation. In step 2206, a real intermediate image 130 of the retina 128 is formed through the objective 104 between the objective 104 and the camera unit 106 in a path 132 of the imaging radiation with the optical radiation reflected from the retina 128. In step 2206, the optical radiation from the retina 128 is directed to the camera unit 106 by the beam splitter 102. In step 2208, the path 134 of the illumination radiation and the path 132 of the imaging radiation are deviated in a predetermined manner by the beam splitter 102 for preventing an overlap of the images of the exit pupil 112 and the entrance pupil 114 at least on the surfaces 125, 126 of the crystalline lens 124. In step 2210, a real image of the intermediate image 130 is formed on a detecting component 136 with the optical radiation reflected from the retina 128 by a relay lens system 138 for transforming the optical image into an electric form to be shown on the screen 150.

An image processing unit 148 may include a processor, controller or the like connected to a memory and to various interfaces of the examination instrument. Generally, the image processing unit 148 may be a central processing unit or an additional operation processor. The processor may comprise an application-specific integrated circuit (ASIC), a field-programmable gate array (FPGA), and/or other hardware components that have been programmed to carry out one or more functions of at least one embodiment. A processor may be realized as an electric circuit of a digital state machine performing logic operations on the basis of instructions of a computer program. In an example embodiment, the at least one processor may be implemented as a microprocessor implementing functions of a central processing unit (CPU) on an integrated circuit. The CPU is a logic state machine executing a computer program, which comprises the program instructions. The instructions may be coded as a computer program using a programming language, which may be a high-level programming language. The CPU may comprise a set of registers, an arithmetic logic unit (ALU), and a control unit (CU). The control unit is controlled by a sequence of instructions transferred to the CPU from the working memory. The control unit may contain a number of microinstructions for basic operations. The implementation of the microinstructions may vary, depending on the CPU design. The microprocessor may also have an operating system (a dedicated operating system of an embedded system, or a real-time operating system), which may provide the computer program with system services. In an embodiment, the one or more memories may further store instructions, that, when executed by the one or more processors, cause the examination instrument to perform its operations.

The memory may include volatile and/or non-volatile memory and typically stores content, data, or the like. For example, the memory may store computer program code such as software applications or operating systems, information, data, content, or the like for the processor to perform steps associated with operation of the apparatus in accordance with embodiments. The memory may be, for example, random access memory (RAM), a hard drive, or other fixed data memory or a storage device. Further, the memory, or part of it, may be removable memory detachably connected to the apparatus.

The data storage medium or the memory unit may be implemented within the processor/computer or external to the processor/computer, in which case it can be communicatively coupled to the processor/computer via various means as is known in the art.

The image data formed by the image processing unit 148 may be saved in a memory 152 of the optical system. Additionally or alternatively, the image data may be stored in a data bank 154 of a hospital's patient data system. An image stored in the memory 152 or in the data bank 154 may be retrieved for a review in the optical system or in a computer.

The examination instrument may be used as a portable ophthalmoscope and/or a portable fundus camera. The reason for that is that the examination instrument may be made compact and light enough to be hand-held during the examination of an eye.

It will be obvious to a person skilled in the art that, as technology advances, the inventive concept can be implemented in various ways. The invention and its embodiments are not limited to the examples described above but may vary within the scope of the claims.

What is claimed is:

1. An apparatus for imaging an eye, comprising:
an illumination unit;
a beam splitter;
an objective;
a relay lens system;
a fixation target unit; and
a camera unit,
the illumination unit comprising an optical radiation source, the illumination unit being configured to direct optical radiation of the source from an exit pupil of the illumination unit to the beam splitter,
the beam splitter being configured to direct the optical radiation to the objective for illuminating the retina of an eye,
the fixation target unit being configured to illuminate the retina of the eye with at least one fixation target image with visible optical radiation;
the objective being configured to form a real intermediate image of the retina between the objective and the camera unit with the optical radiation reflected from the retina, wherein a real image of the exit pupil of the illumination unit and a real image of an entrance pupil of the camera unit are formable in the position ranging from the cornea to the backside of the crystalline lens of an eye,
the beam splitter residing between the objective and the aperture of the relay lens system and being configured to direct the optical radiation from the retina to the camera unit, the beam splitter being configured to deviate the path of the illumination radiation and the path of the imaging radiation in a predetermined manner for preventing an overlap of the images of the exit pupil and the entrance pupil at least in the crystalline lens, and
the camera unit comprising a detecting component, the relay lens system being configured to form a real image of the intermediate image on the detecting component with the optical radiation reflected from the retina for the optical image to be shown.

2. The apparatus of claim 1, wherein the fixation target unit is configured to direct optical radiation to the beam splitter which is configured to direct the optical radiation from the fixation target unit to the objective for forming at least one image associated with the fixation target unit on the retina.

3. The apparatus of claim 1, wherein the objective is configured to form a real image of the exit pupil of the fixation target unit at least approximately in the position ranging from the cornea to the back side of the crystalline lens of the eye.

4. The apparatus of claim 1, wherein the detecting component is configured to transform the optical image into an electric form.

5. The apparatus of claim 1, wherein the beam splitter comprises at least one polarizer.

6. The apparatus of claim 1, wherein the objective is configured to form the real image of the exit pupil of the illumination unit substantially inside the crystalline lens.

7. The apparatus of claim 1, wherein the objective is configured to form the real image of the entrance pupil of the camera unit substantially inside the crystalline lens.

8. The apparatus of claim 1, wherein the real image of the exit pupil of the illumination unit and the real image of the entrance pupil of the camera unit is in different places on a line parallel to the optical axis of the path of the illumination radiation or the path of the imaging radiation.

9. The apparatus of claim 1, wherein the illumination unit is configured to illuminate the retina continuously with infrared radiation and the illumination unit is configured to flash visible light for capturing at least one still image of the retina.

10. The apparatus of claim 1, wherein the beam splitter resides between the objective and the aperture of the relay lens system.

11. The apparatus of claim 1, wherein a set comprises the camera unit and a plurality of optical functional parts,
the optical functional parts being repeatedly attachable to and detachable from the camera unit,
the camera unit alone being configured to capture images of at least one organ on the outer surface of a body,
one of the optical functional parts comprising the beam splitter and the objective for imaging the eye; and
the camera unit with at least one further optical functional part in the set being configured to capture images of at least one organ different from the eye and the at least one organ on the outer surface of a body.

12. A method for imaging an eye comprising:
directing optical radiation of a source from an exit pupil of an illumination unit to a beam splitter;

directing, by the beam splitter, the optical radiation to an objective along a path of the illumination radiation;

illuminating, the fixation target unit, the retina of the eye with at least one fixation target image with visible optical radiation;

illuminating the retina of the eye through the objective with the optical radiation such that a real image of the exit pupil of the illumination unit and a real image of an entrance pupil of a camera unit are formable in a position ranging from the cornea to the backside of the crystalline lens of the eye;

forming, through the objective, a real intermediate image of the retina between the objective and the camera unit in a path of the imaging radiation with the optical radiation reflected from the retina;

directing, by the beam splitter, the optical radiation from the retina to the camera unit;

deviating the path of the illumination radiation and the path of the imaging radiation in a predetermined manner between the objective and the aperture of the relay lens system by the beam splitter for preventing an overlap of the images of the exit pupil and the entrance pupil at least on the surfaces of the crystalline lens; and forming, by a relay lens system, a real image of the intermediate image on a detecting component with the optical radiation reflected from the retina for the optical image to be shown.

13. The method of claim 12, the method further comprising directing, by the fixation target unit, optical radiation to the beam splitter and directing by the beam splitter the optical radiation from the fixation target unit to the objective for forming at least one image associated with the fixation target unit on the retina.

14. The method of claim 12, the method further comprising forming, by the objective, a real image of the exit pupil of the fixation target unit at least approximately in the position ranging from the cornea to the back side of the crystalline lens of the eye.

15. The method of claim 12, the method further comprising transforming, by the detecting component, the optical image into an electric form.

16. The method of claim 12, the method further comprising directing the optical radiation by a polarization beam splitter.

17. The method of claim 12, the method further comprising forming, by the objective, the real image of the exit pupil of the illumination unit inside the crystalline lens.

18. The method of claim 12, the method further comprising forming, by the objective, the real image of the entrance pupil of the camera unit substantially inside the crystalline lens.

19. The method of claim 12, the method further comprising forming the real image of the exit pupil of the illumination unit and the real image of the entrance pupil of the camera unit in different places on a line parallel to the optical axis of the path of the illumination radiation or the path of the imaging radiation.

20. The method of claim 12, the method further comprising illuminating the retina continuously with infrared radiation and flashing visible light for capturing at least one still image of the retina.

21. The method of claim 12, wherein the beam splitter residing between the objective and the aperture of the relay lens system forms a deviation between the illuminating optical radiation and the imaging radiation in a place different from the relay lens system.

22. The method of claim 12, wherein a set comprises the camera unit and a plurality of optical functional parts, the optical functional parts being repeatedly attachable to and detachable from the camera unit, the camera unit alone being configured to capture images of at least one organ on the outer surface of a body, one of the optical functional parts comprising the beam splitter and the objective for imaging the eye, and the camera unit with at least one further optical functional part in the set being capable to capture images of at least one organ different from both the eye and the at least one organ on the outer surface of a body.

* * * * *